US012788345B2

(12) United States Patent
Yokoi

(10) Patent No.: US 12,788,345 B2
(45) Date of Patent: Nov. 10, 2026

(54) PHOTON COUNTING CT APPARATUS CONFIGURED TO USE A CALIBRATION MEMBER, AND SUBSTANCE DECOMPOSITION METHOD

(71) Applicant: FUJIFILM Healthcare Corporation, Kashiwa (JP)

(72) Inventor: Kazuma Yokoi, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 201 days.

(21) Appl. No.: 18/645,647

(22) Filed: Apr. 25, 2024

(65) Prior Publication Data

US 2024/0377545 A1 Nov. 14, 2024

(30) Foreign Application Priority Data

May 9, 2023 (JP) ................................ 2023-077106

(51) Int. Cl.
*A61B 6/03* (2006.01)
*A61B 6/00* (2006.01)
(Continued)

(52) U.S. Cl.
CPC .............. *A61B 6/482* (2013.01); *A61B 6/032* (2013.01); *A61B 6/40* (2013.01); *A61B 6/4035* (2013.01);
(Continued)

(58) Field of Classification Search
CPC ....... A61B 6/032; A61B 6/035; A61B 6/4035; A61B 6/42; A61B 6/4208; A61B 6/4241;
(Continued)

(56) References Cited

U.S. PATENT DOCUMENTS 4,991,189 A * 2/1991 Boomgaarden ...... A61B 6/5258 378/19
4,995,107 A * 2/1991 Klingenbeck ............ H05G 1/60 378/7

(Continued)

FOREIGN PATENT DOCUMENTS

CN 113100800 A 7/2021
CN 114720493 A 7/2022

(Continued)

OTHER PUBLICATIONS

Chinese official action (and English-language translation thereof of) dated Nov. 19, 2025 in connection with Chinese Patent Application No. 2024105543402.

(Continued)

*Primary Examiner* — Allen C. Ho

(57) ABSTRACT

A photon counting CT apparatus and a substance decomposition method can be provided. A storage unit is configured to acquire an energy spectrum of an X-ray transmitted through a calibration member in which a first base substance and a second base substance are combined, while changing a thickness of the first base substance and a thickness of the second base substance, with a reference X-ray dose, and store the energy spectrum as calibration data in advance. A correction table creation unit acquires the energy spectrum of the X-ray transmitted through the calibration member while changing the thickness of the first base substance, thickness of the second base substance, and X-ray dose, and creates a correction table indicating a relationship between the number of X-ray photons and the X-ray dose for each energy bin. An image generation unit generates a tomographic image decomposed for each substance based on the calibration data and the correction table.

8 Claims, 9 Drawing Sheets

(51) Int. Cl.
*A61B 6/40* (2024.01)
*A61B 6/42* (2024.01)
*A61B 6/58* (2024.01)
*G01T 1/17* (2006.01)
*G01T 7/00* (2006.01)

(52) U.S. Cl.
CPC .......... *A61B 6/4241* (2013.01); *A61B 6/5205* (2013.01); *A61B 6/582* (2013.01); *A61B 6/583* (2013.01); *A61B 6/585* (2013.01); *G01T 1/17* (2013.01); *G01T 7/005* (2013.01)

(58) Field of Classification Search
CPC ....... A61B 6/4266; A61B 6/4275; A61B 6/44; A61B 6/4429; A61B 6/4435; A61B 6/482; A61B 6/52; A61B 6/5205; A61B 6/54; A61B 6/542; A61B 6/545; A61B 6/582; A61B 6/583; A61B 6/585
USPC .... 378/5–7, 16, 19, 62, 98.9, 196–198, 207; 250/370.09, 252.1
See application file for complete search history.

(56) References Cited

U.S. PATENT DOCUMENTS 5,131,021 A * 7/1992 Gard .................... G21K 1/025 378/146
5,155,365 A * 10/1992 Cann .................... A61B 6/4241 250/363.04
5,400,387 A * 3/1995 Gard .................... H05G 1/265 378/207
5,473,663 A * 12/1995 Hsieh .................... A61B 6/585 378/207
5,583,903 A * 12/1996 Saito .................... A61B 6/4021 378/19
5,684,855 A * 11/1997 Aradate .................... A61B 6/032 378/7
6,735,273 B2 * 5/2004 Flohr .................... A61B 6/405 378/158
6,813,333 B2 * 11/2004 Karau .................... A61B 6/032 378/19
6,898,263 B2 * 5/2005 Avinash .................... A61B 6/032 378/4
6,925,140 B2 * 8/2005 Bruder .................... A61B 6/4233 378/7
6,950,493 B2 * 9/2005 Besson .................... A61B 6/032 378/16
6,987,833 B2 * 1/2006 Du .................... A61B 6/482 378/53
6,999,549 B2 * 2/2006 Sabol .................... A61B 6/482 378/5
7,149,278 B2 * 12/2006 Arenson .................... A61B 6/4241 378/19
7,209,536 B2 * 4/2007 Walter .................... A61B 6/4042 378/5
7,466,793 B2 * 12/2008 Wu .................... A61B 6/482 378/19
7,583,779 B2 * 9/2009 Tkaczyk .................... A61B 6/482 378/4
7,756,239 B2 * 7/2010 Wu .................... A61B 6/482 378/4
7,778,380 B2 * 8/2010 Altman .................... A61B 6/482 378/4
8,160,206 B2 * 4/2012 Wu .................... A61B 6/482 382/130
8,315,352 B2 * 11/2012 Wu .................... A61B 6/583 378/207
8,363,917 B2 * 1/2013 Fan .................... G06T 11/008 378/57
9,052,266 B2 * 6/2015 Miyazaki .................... A61B 6/4241
9,155,516 B2 * 10/2015 Wang .................... A61B 6/583
9,750,471 B2 * 9/2017 Schirra .................... A61B 6/583
9,841,389 B2 * 12/2017 Tamura .................... A61B 6/482
9,924,916 B2 * 3/2018 Kato .................... A61B 6/482
10,074,197 B2 * 9/2018 Nitta .................... A61B 6/4241
10,117,628 B2 * 11/2018 Tamura .................... A61B 6/482
10,139,354 B2 * 11/2018 Persson .................... A61B 6/482
10,219,763 B2 * 3/2019 Kojima .................... A61B 6/032
10,281,592 B2 * 5/2019 Kawata .................... A61B 6/482
10,451,568 B2 * 10/2019 Moriyasu .................... A61B 6/482
10,507,005 B2 * 12/2019 Jin .................... A61B 6/482
10,542,947 B2 * 1/2020 Kojima .................... A61B 6/032
10,779,778 B2 * 9/2020 Rui .................... A61B 6/4233
11,009,470 B2 * 5/2021 Yamakawa .................... A61B 6/584
11,096,641 B2 * 8/2021 Yokoi .................... A61B 6/4241
11,229,413 B1 * 1/2022 Lai .................... A61B 6/4241
11,249,035 B2 * 2/2022 Zhan .................... A61B 6/582
11,337,671 B2 * 5/2022 Fan .................... A61B 6/482
11,644,587 B2 * 5/2023 Zhan .................... A61B 6/4241 378/207
11,653,892 B2 * 5/2023 Zhan .................... A61B 6/583 378/207
11,896,410 B2 * 2/2024 Kojima .................... A61B 6/032
11,944,468 B2 * 4/2024 Kojima .................... A61B 6/582
11,944,484 B2 * 4/2024 Zhan .................... A61B 6/032
12,053,321 B2 * 8/2024 Yokoi .................... A61B 6/583
12,102,471 B2 * 10/2024 Zhan .................... A61B 6/482
12,121,380 B2 * 10/2024 Kojima .................... A61B 6/5205
12,144,663 B2 * 11/2024 Yokoi .................... A61B 6/5258
12,193,857 B2 * 1/2025 Fan .................... A61B 6/4241
12,408,888 B2 * 9/2025 Zhan .................... A61B 6/585
12,453,520 B2 * 10/2025 Cederström .................... G01T 7/005
12,533,092 B2 * 1/2026 Tsukagoshi .................... A61B 6/482
12,622,666 B2 * 5/2026 Takahashi .................... A61B 6/583
12,629,109 B2 * 5/2026 Kim .................... A61B 6/482
12,650,393 B2 * 6/2026 Loberg .................... A61B 6/482
12,653,470 B2 * 6/2026 Zhan .................... A61B 6/482
2019/0021685 A1 1/2019 Kojima et al.
2021/0212646 A1 7/2021 Yokoi
2022/0211338 A1 7/2022 Kojima
2022/0395248 A1 12/2022 Yokoi

FOREIGN PATENT DOCUMENTS

CN 115530860 A 12/2022
JP 6564330 B2 8/2019
JP 2019-176988 A 10/2019

OTHER PUBLICATIONS

English-language translation of Chinese official action dated Aug. 15, 2025 in connection Chinese Patent Application No. 202410554340.2.

* cited by examiner

PHOTON COUNTING CT APPARATUS CONFIGURED TO USE A CALIBRATION MEMBER, AND SUBSTANCE DECOMPOSITION METHOD

CROSS-REFERENCE TO RELATED APPLICATION

The present application claims priority from Japanese Patent Application JP 2023-077106 filed on May 9, 2023, the content of which is hereby incorporated by reference into this application.

BACKGROUND OF THE INVENTION

1. Field of the Invention

The present invention relates to a photon counting CT apparatus that is an X-ray computed tomography (CT) apparatus comprising a photon counting type detector, and a substance decomposition method.

2. Description of the Related Art

The X-ray CT apparatus is an apparatus that generates a tomographic image of a subject by using a plurality of pieces of projection data acquired by performing irradiation of the subject with X-rays and detection of the X-rays transmitted through the object at a plurality of projection angles. In a photon counting CT apparatus using a photon counting type detector for detecting X-rays, a tomographic image decomposed into substances having different composition, for example, a tomographic image decomposed into an iodine contrast medium used for angiography and soft tissue can be obtained.

A dose of X-rays emitted to a subject fluctuates over time, and the fluctuation over time in the X-ray dose causes an artifact in a tomographic image generated by an X-ray CT apparatus. Therefore, the projection data is corrected using reference data including the fluctuation over time in the X-ray dose acquired by a reference detector that detects X-rays not transmitted through the subject, whereby the artifact of the tomographic image is suppressed. In the photon counting CT apparatus, since an amount of pile-up also increases as a dose rate of X-rays increases, it is necessary to identify (calibrate) a spectral change due to pile-up for correcting the projection data with the reference data.

JP6564330B discloses a photon counting CT apparatus that acquires in advance how a detection signal of a reference detector is changed in a case where a dose rate of X-rays is changed, and corrects a detection error due to pile-up based on the acquired data. That is, since the detection signal of the reference detector is decreased as an amount of pile-up is increased in a case where the dose rate of X-rays is increased, a degree of decrease in the detection signal with respect to the increase in the dose rate is used for correcting the detection error due to pile-up.

SUMMARY OF THE INVENTION

However, in JP6564330B, there is no consideration for the fact that the amount of pile-up changes depending on a difference in radiation quality of X-rays. In X-rays incident on each channel of the photon counting type detector, the dose rate changes in accordance with a transmission path in the subject, and the radiation quality also changes. Since the amount of pile-up is increased or decreased not only by the dose rate but also by the change in radiation quality, accuracy of the substance decomposition is reduced in a case where influence of the change in radiation quality is not included.

Therefore, an object of the present invention is to provide a photon counting CT apparatus and a substance decomposition method capable of reducing influence of pile-up that changes depending on a difference in radiation quality of X-rays.

In order to achieve the above object, according to an aspect of the present invention, a photon counting CT apparatus provided with an X-ray source that irradiates a subject with an X-ray, a photon counting type detector that detects the X-ray and outputs a signal corresponding to photon energy of the X-ray, and an image generation unit that generates a tomographic image of the subject based on the signal output by the photon counting type detector, the photon counting CT apparatus comprises a storage unit configured to acquire an energy spectrum of an X-ray transmitted through a calibration member in which a first base substance and a second base substance, which are known substances, are combined, while changing a thickness of the first base substance and a thickness of the second base substance, with a reference X-ray dose, and store the energy spectrum as calibration data in advance; a correction table creation unit configured to acquire the energy spectrum of the X-ray transmitted through the calibration member while changing the thickness of the first base substance, the thickness of the second base substance, and the X-ray dose, and create a correction table indicating a relationship between the number of X-ray photons and the X-ray dose for each energy bin; and an image generation unit configured to generate a tomographic image decomposed for each substance based on the calibration data and the correction table.

In addition, according to an aspect of the present invention, a substance decomposition method using a photon counting CT apparatus provided with an X-ray source that irradiates a subject with an X-ray, a photon counting type detector that detects the X-ray and outputs a signal corresponding to photon energy of the X-ray, and an image generation unit that generates a tomographic image of the subject based on the signal output by the photon counting type detector, the substance decomposition method comprises acquiring an energy spectrum of an X-ray transmitted through a calibration member in which a first base substance and a second base substance, which are known substances, are combined, while changing a thickness of the first base substance and a thickness of the second base substance, with a reference X-ray dose, and storing the energy spectrum as calibration data in advance; acquiring the energy spectrum of the X-ray transmitted through the calibration member while changing the thickness of the first base substance, the thickness of the second base substance, and the X-ray dose, and creating a correction table indicating a relationship between the number of X-ray photons and the X-ray dose for each energy bin; and generating a tomographic image decomposed for each substance based on the calibration data and the correction table.

According to the present invention, it is possible to provide the photon counting CT apparatus and the substance decomposition method capable of reducing the influence of pile-up that changes depending on the difference in the radiation quality of the X-rays.

DESCRIPTION OF THE PREFERRED EMBODIMENTS

Figure 1:
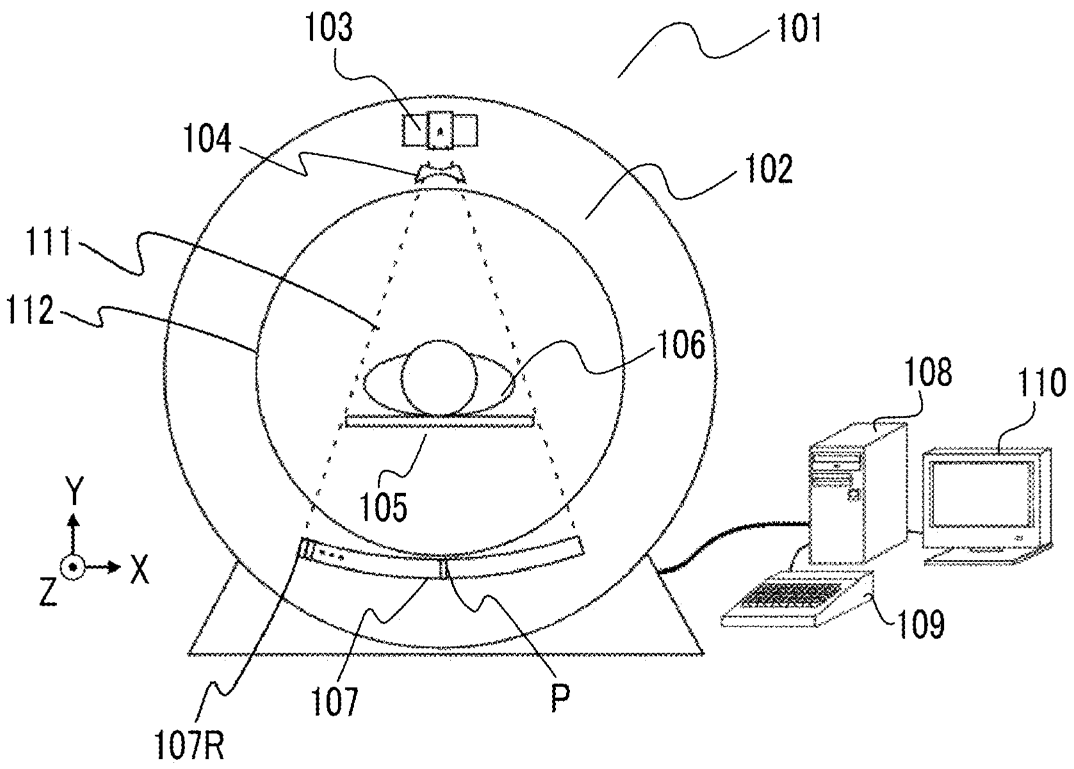
FIG. 1 is a diagram showing an overall configuration of a PCCT apparatus.

Hereinafter, a photon counting CT apparatus and a substance decomposition method according to an embodiment of the present invention will be described with reference to the drawings. In the following description and the accompanying drawings, components having the same functional configuration are designated by the same reference numerals, and thus duplicate description thereof will not be repeated.

Example 1

FIG. 1 is an overall configuration diagram of a photon counting CT apparatus 101 of the present example. A lateral direction of the drawing is defined as an X-axis, a longitudinal direction of the drawing is defined as a Y-axis, and a direction orthogonal to an XY plane is defined as a Z-axis. The photon counting CT apparatus 101 comprises a gantry 102, an X-ray tube 103, a bow tie filter 104, a bed 105, a detector panel 107, an operation device 108, an input device 109, and a display device 110.

A subject 106 is placed on the bed 105 and is disposed in an opening portion 112 provided in the gantry 102. X-rays 111 emitted from the X-ray tube 103 are formed into a beam shape suitable for a size of the subject 106 by the bow tie filter 104, are emitted to the subject 106, are transmitted through the subject 106, and are detected by the detector panel 107. The X-ray tube 103 and the detector panel 107 are attached to the gantry 102 so as to face each other with the subject 106 interposed therebetween, and are rotated around the subject 106 by a rotation drive unit of the gantry 102. The irradiation with the X-rays from the X-ray tube 103 and the X-ray measurement by the detector panel 107 are repeated with the rotation of both the X-ray tube 103 and the detector panel 107, and thus projection data at various projection angles is acquired.

The acquired projection data is subjected to image reconstruction processing by the operation device 108, whereby a tomographic image of the subject 106 is generated and displayed on the display device 110. In addition, in a case where the projection data is acquired while the bed 105 on which the subject 106 is placed and the gantry 102 are relatively moved in a Z-axis direction, a volume image of the subject 106 is generated. An X-ray dose of X-rays emitted from the X-ray tube 103, a rotation speed of the gantry 102, and a relative movement speed between the gantry 102 and the bed 105 are set based on a scan condition input by an operator through the input device 109. In addition, the operation device 108 has a hardware configuration similar to a general computer device, and comprises a central processing unit (CPU), a memory, a hard disk drive (HDD), and the like, and performs correction processing on the projection data and the like and control of each unit.

The detector panel 107 is configured by disposing a plurality of detection elements P in an arc shape centered on an X-ray focus of the X-ray tube 103. In addition, a reference detector 107R that detects X-rays not transmitted through the subject 106 is provided at an end part of the detector panel 107. Since reference data obtained by the reference detector 107R includes a fluctuation over time in the X-ray dose of X-rays emitted to the subject 106, the reference data is used for correcting the fluctuation over time in the X-ray dose.

Figure 2:
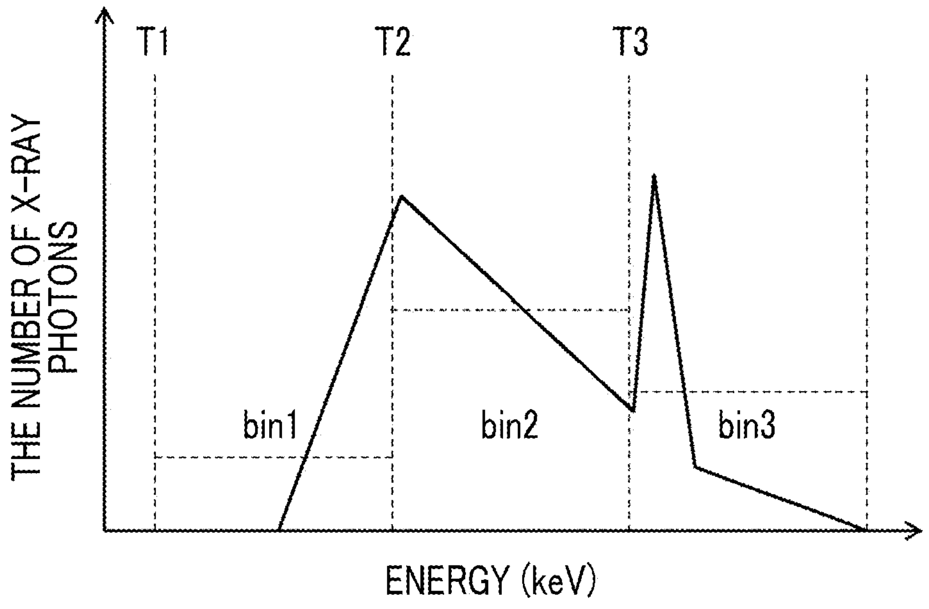
FIG. 2 is a diagram showing an example of X-rays divided into a plurality of energy bins.

In a case where the detection element P is a photon counting type detector, incident X-ray photons are individually counted, and energy of the X-ray photons is measured. FIG. 2 shows the number of X-ray photons divided and counted in three energy bins bin1, bin2, and bin3 which are respectively from T1 to T2, from T2 to T3, and from T3.

In the photon counting CT apparatus 101 comprising the photon counting type detector, a photon energy spectrum related to the projection data of the subject 106 can be acquired, so that it is possible to generate a medical image decomposed into substances having different composition or a medical image divided into a plurality of energy components. In order to obtain a medical image or the like decomposed into substances having different composition, it is necessary to calibrate a relationship between an output and photon energy in a case where a combination of a plurality of base substances having known composition and thicknesses is measured by a photon counting type detector, for each detection element.

Figure 3:
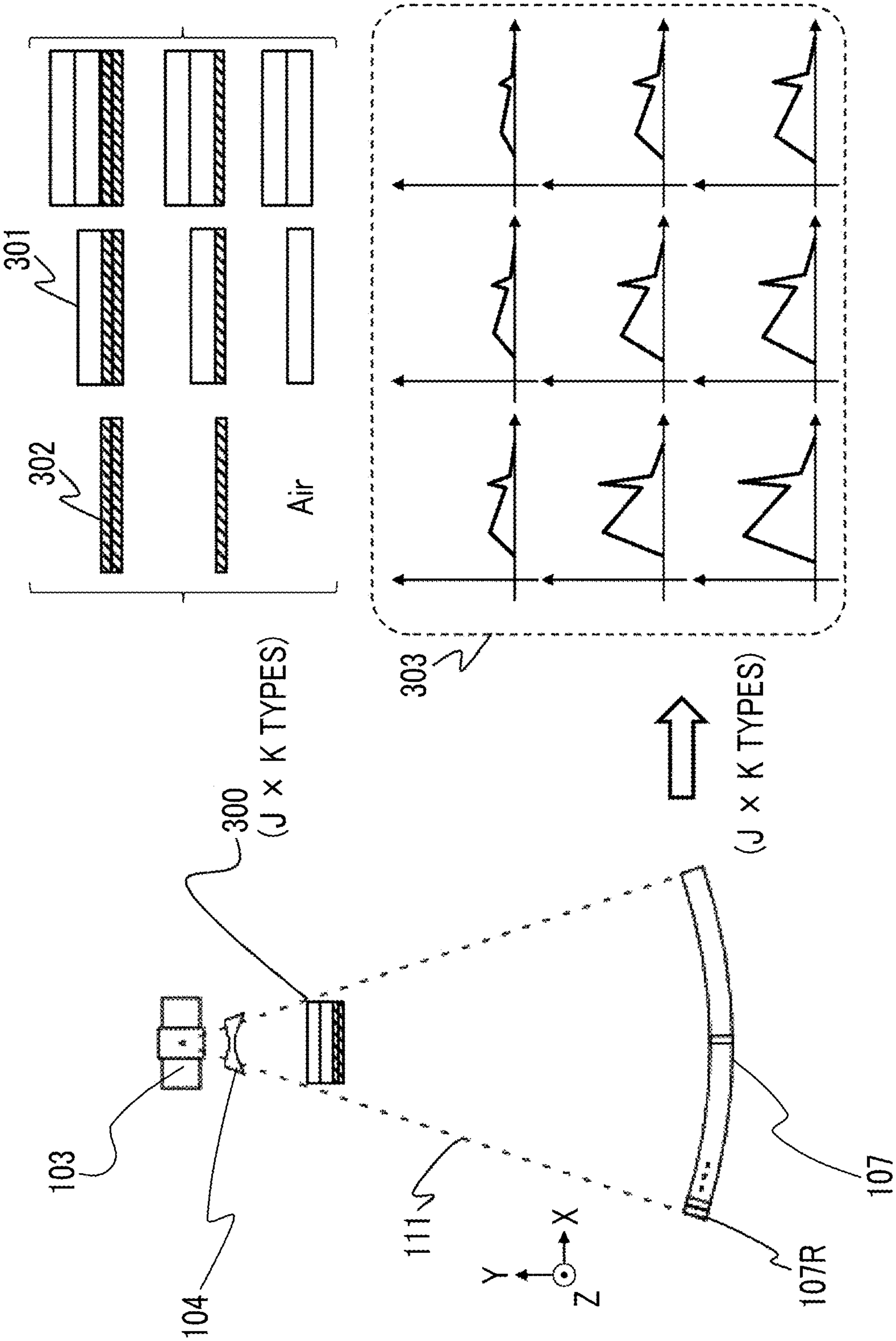
FIG. 3 is a diagram describing calibration of a photon counting type detector.

The calibration of the photon counting type detector will be described with reference to FIG. 3. For the calibration of the photon counting type detector, a calibration member 300 in which a plurality of base substances having known composition and thicknesses are combined is used. As the calibration member 300, for example, combinations of a first base substance 301 and a second base substance 302, which are a plurality of plates of each of the base substances having different thicknesses, are used. For example, in a case where there are J types of thicknesses for the first base substance 301 and there are K types of thicknesses for the second base substance 302, J×K types of calibration members 300 are used, and an energy spectrum of X-rays transmitted through each of the calibration members 300 is acquired as calibration data 303 for each detection element. In FIG. 3, since J=3 and K=3, nine types of energy spectra are shown as calibration data 303. The acquired calibration data 303 is stored in a storage unit of the operation device 108 and is used for calibrating the projection data of the subject 106.

Since the amount of pile-up is increased in a case where the X-ray dose emitted to the calibration member 300 is increased, the energy spectrum of the X-rays transmitted through the calibration member 300 is changed also depending on the X-ray dose. Therefore, in the present invention, a correction table used for correcting the calibration data 303 or the projection data of the subject 106 is created based on the energy spectrum acquired while changing the X-ray dose of X-rays emitted to the calibration member 300.

Figure 4:
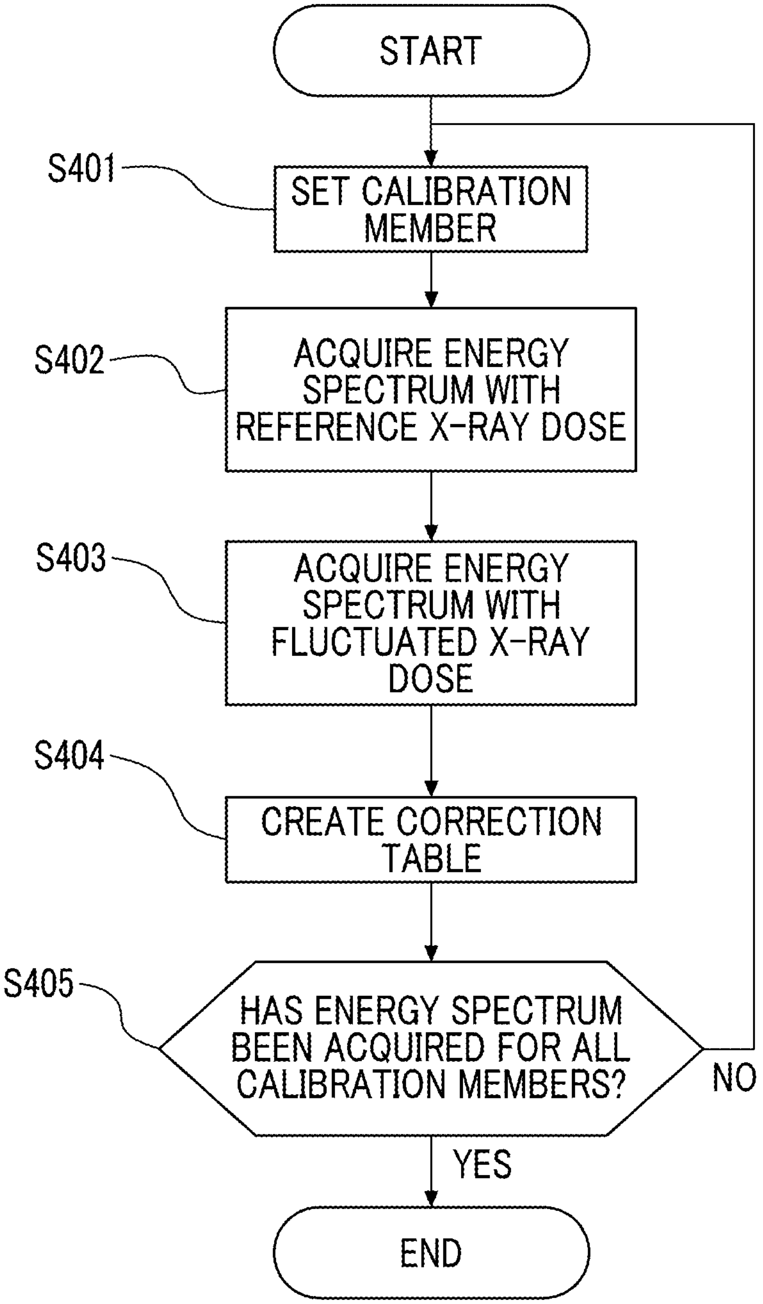
FIG. 4 is a diagram showing an example of a flow of processing of creating a correction table.

An example of a flow of processing of creating the correction table will be described step by step with reference to FIG. 4.

S401

The calibration member 300, which is a combination of the first base substance 301 and the second base substance 302, is set in the opening portion 112. The composition and the thickness of the first base substance 301 and the second base substance 302 are known, and for example, acrylic is used for the first base substance 301 and aluminum is used for the second base substance 302.

S402

Through the control of the operation device 108, the energy spectrum of the X-rays transmitted through the calibration member 300 set in S401 is acquired with a reference X-ray dose. More specifically, in a state where the gantry 102 is stationary, the X-ray tube 103 in which a tube current, which is a reference value, is set irradiates the calibration member 300 with X-rays, and the X-rays transmitted through the calibration member 300 are detected by the detector panel 107, so that the energy spectrum is acquired for each detection element. The acquired energy spectrum is stored in the storage unit as the calibration data 303. In the reference detector 107R, the X-rays not transmitted through the calibration member 300 are detected and stored in the storage unit in association with the calibration data 303.

S403

Through the control of the operation device 108, the energy spectrum of the X-rays transmitted through the calibration member 300 set in S401 is acquired with the X-ray dose fluctuated from the reference. More specifically, the energy spectrum is acquired for each detection element through the irradiation with the X-rays from the X-ray tube 103 in which a tube current different from the reference value is set and the X-ray detection performed by the detector panel 107. In the reference detector 107R, the X-rays not transmitted through the calibration member 300 are detected as in S402. The tube current set in S403 is preferably in a range corresponding to the fluctuation over time in the X-ray dose, for example, in a range of 295 mA to 305 mA in a case where the reference value of the tube current is 300 mA. By setting the tube current in the range corresponding to the fluctuation over time in the X-ray dose, the fluctuation over time in the X-ray dose can be more accurately corrected.

S404

The operation device 108 creates the correction table using the energy spectra acquired in S402 and S403. The correction table shows a relationship between the number of X-ray photons and the X-ray dose for each energy bin. The created correction table is stored in the storage unit.

Figure 5:
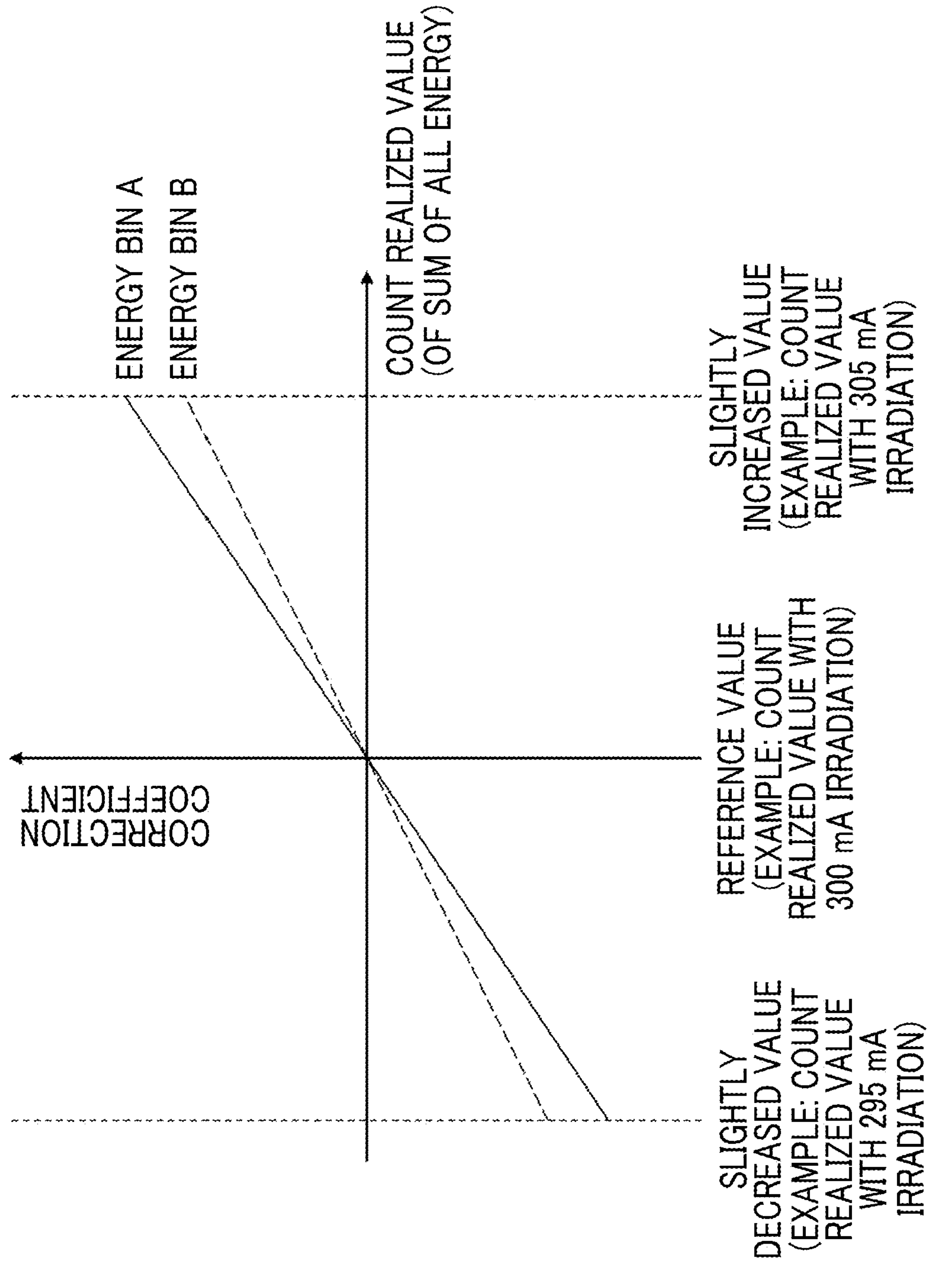
FIG. 5 is a diagram describing an example of the correction table.

An example of the correction table will be described with reference to FIG. 5. The correction table illustrated in FIG. 5 has a correction coefficient on a vertical axis and a count realized value on a lateral axis. The count realized value is an actual measured value of the number of X-ray photons in a case where the irradiation with X-rays is performed at the tube currents set in S402 and S403. The correction coefficient is a value obtained by dividing the number of X-ray photons counted in each count realized value by the number of X-ray photons in a case where the count realized value is a reference value, and is obtained for each energy bin. That is, the correction coefficient indicates 1 in a case where the count realized value is the reference value, the correction coefficient indicates a value greater than 1 in a case where the count realized value is a slightly increased value, and the correction coefficient indicates a value smaller than 1 in a case where the count realized value is a slightly decreased value.

The correction table is created for each detection element in the number of types of the calibration member 300. In addition, the correction table may be an equation obtained by linear approximation or quadratic curve approximation of the number of respective X-ray photons counted at different tube currents.

S405

The operation device 108 determines whether or not the energy spectrum has been acquired for all the calibration members 300. In a case where the energy spectrum is acquired for all the calibration members 300, the flow of the processing is ended. Otherwise, the processing returns to S401, and another calibration member 300 is set.

Through the flow of the processing described with reference to FIG. 4, the energy spectrum of the X-rays transmitted through the calibration member 300 is acquired while changing the thickness of the first base substance 301 and the thickness of the second base substance 302, which are known substances, and the X-ray dose emitted to the calibration member 300. Then, based on the acquired energy spectrum, the calibration data 303 and the correction table are stored in the storage unit, and are used for the substance decomposition of the subject 106.

Figure 6:
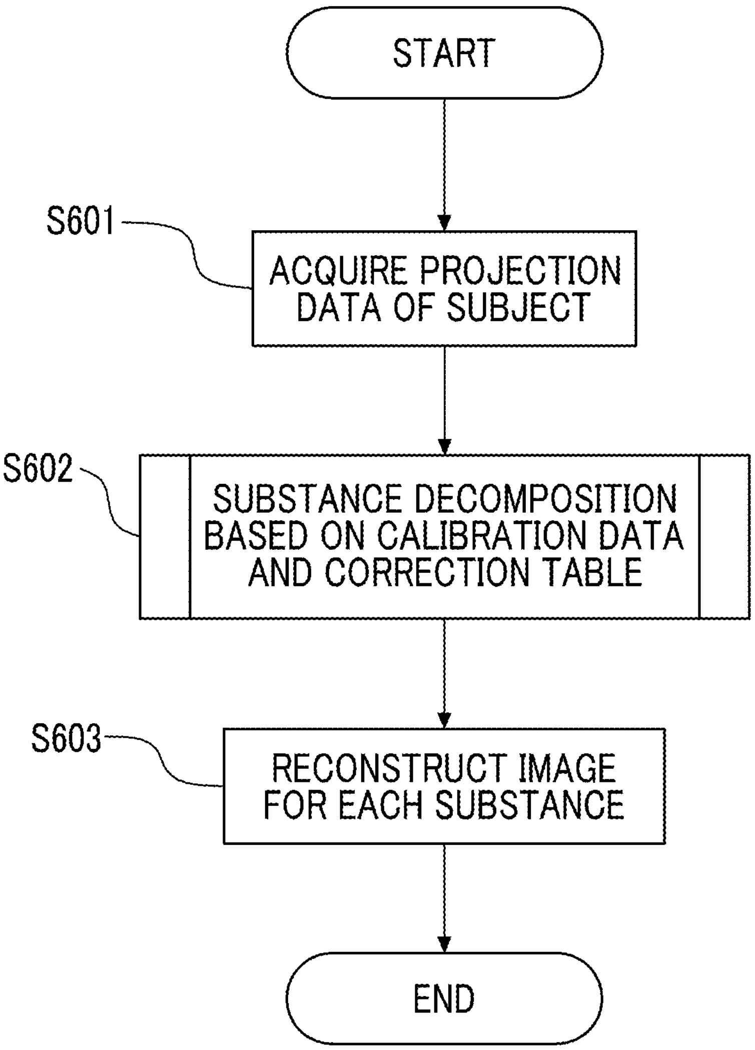
FIG. 6 is a diagram showing an example of a flow of processing of generating a tomographic image decomposed for each substance.

An example of a flow of processing of generating the tomographic image decomposed for each substance on the basis of the calibration data 303 and the correction table will be described step by step with reference to FIG. 6.

S601

Through the control of the operation device 108, the projection data of the subject 106 is acquired. More specifically, in a state where the gantry 102 is rotated, the subject 106 is irradiated with X-rays from the X-ray tube 103, and the X-rays transmitted through the subject 106 are detected by the detector panel 107, and thus the projection data at various projection angles is acquired. The projection data of the subject 106 is acquired while being divided into a plurality of energy bins. In addition, the reference data is acquired together with the projection data of the subject 106. The reference data obtained by detecting the X-rays not transmitted through the subject 106 includes the fluctuation over time in the X-ray dose emitted to the subject 106.

S602

The operation device 108 decomposes the projection data of the subject 106 acquired in S601 into a plurality of substances, for example, the first base substance 301 and the second base substance 302, based on the calibration data 303 and the correction table read from the storage unit.

Figure 7:
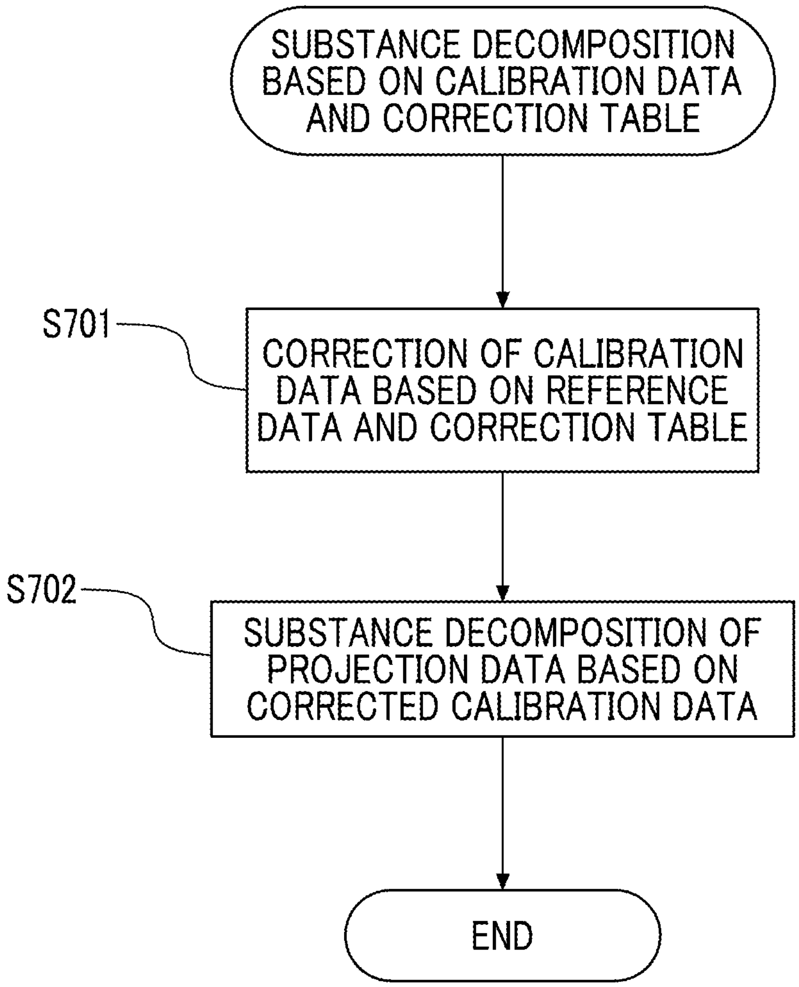
FIG. 7 is a diagram showing an example of a flow of processing of substance decomposition.

An example of the flow of processing of S602 will be described step by step with reference to FIG. 7.

S701

Figure 8:
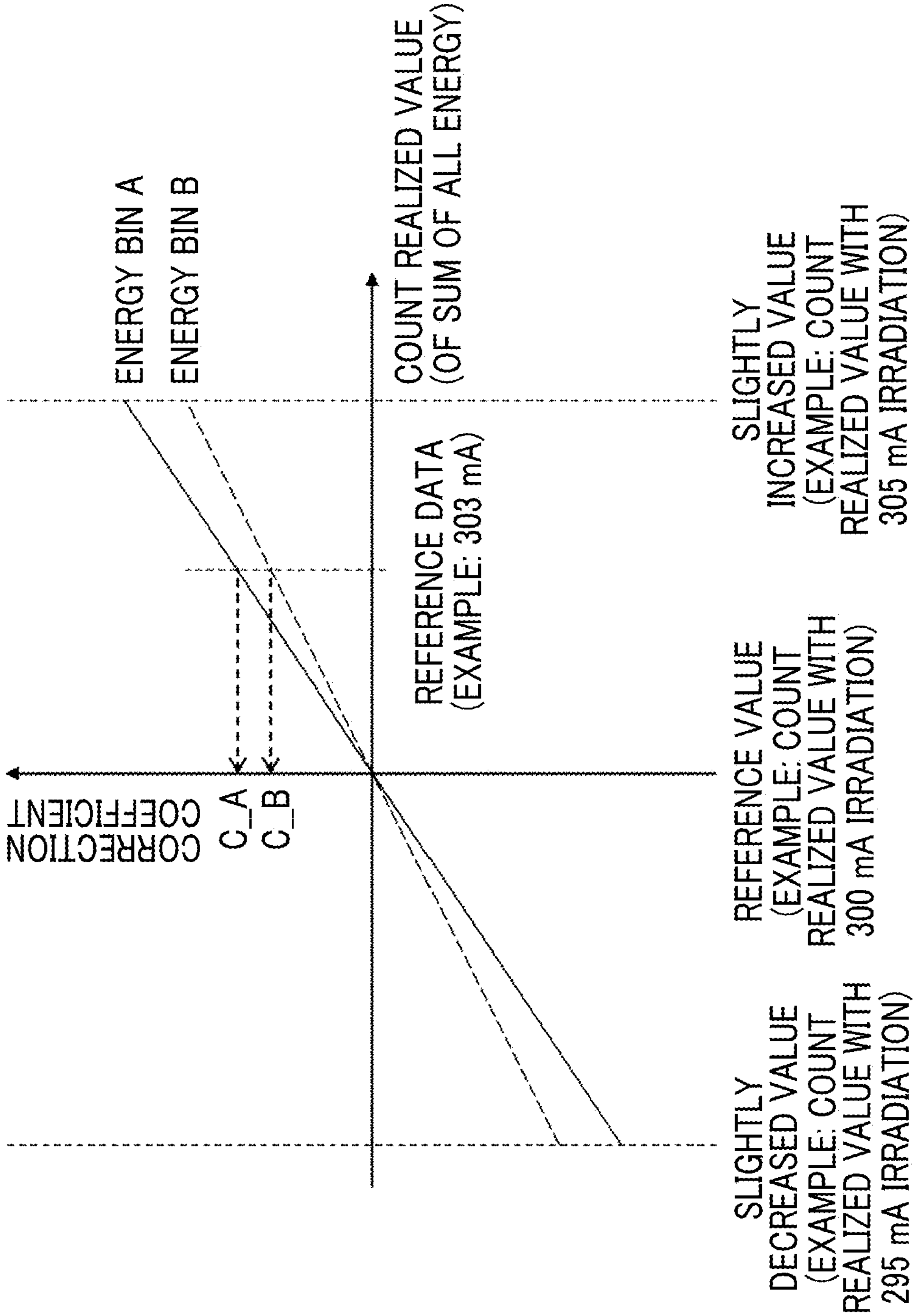
FIG. 8 is a diagram describing correction of calibration data based on reference data.

The operation device 108 corrects the calibration data 303 based on the reference data acquired in S601 and the correction table. For example, as shown in FIG. 8, in a case where the reference data is 303 mA, a correction coefficient C_A of an energy bin A and a correction coefficient C_B of an energy bin B are obtained from the correction table, and the calibration data 303 is corrected based on the correction coefficients C_A and C_B. That is, the calibration data 303 acquired with the reference X-ray dose is corrected by multiplying the number of X-ray photons in the energy bin A by C_A and multiplying the number of X-ray photons in the energy bin B by C_B to calculate the corrected calibration data.

S702

The operation device 108 performs substance decomposition on the projection data of the subject 106 by using the calibration data corrected in S701. Specifically, first, the energy spectrum closest to the energy spectrum of the projection data of the subject 106 is selected from the corrected calibration data. Then, substance decomposition is performed according to the thickness of the first base substance 301 and the thickness of the second base substance 302 corresponding to the selected energy spectrum to generate the projection data of the first base substance 301 and the projection data of the second base substance 302.

By the flow of the processing described with reference to FIG. 7, substance decomposition is performed on the projection data of the subject 106 by using the reference data and the calibration data corrected based on the correction table. Since the calibration data corrected based on the reference data and the correction table is used for the substance decomposition, the influence of pile-up that changes depending on the fluctuation over time in the X-ray dose or the difference in the radiation quality of the X-rays is reduced, and the accuracy of the substance decomposition can be improved. The substance decomposition of S602 based on the calibration data 303 and the correction table is not limited to the flow of the processing of FIG. 7.

Figure 9:
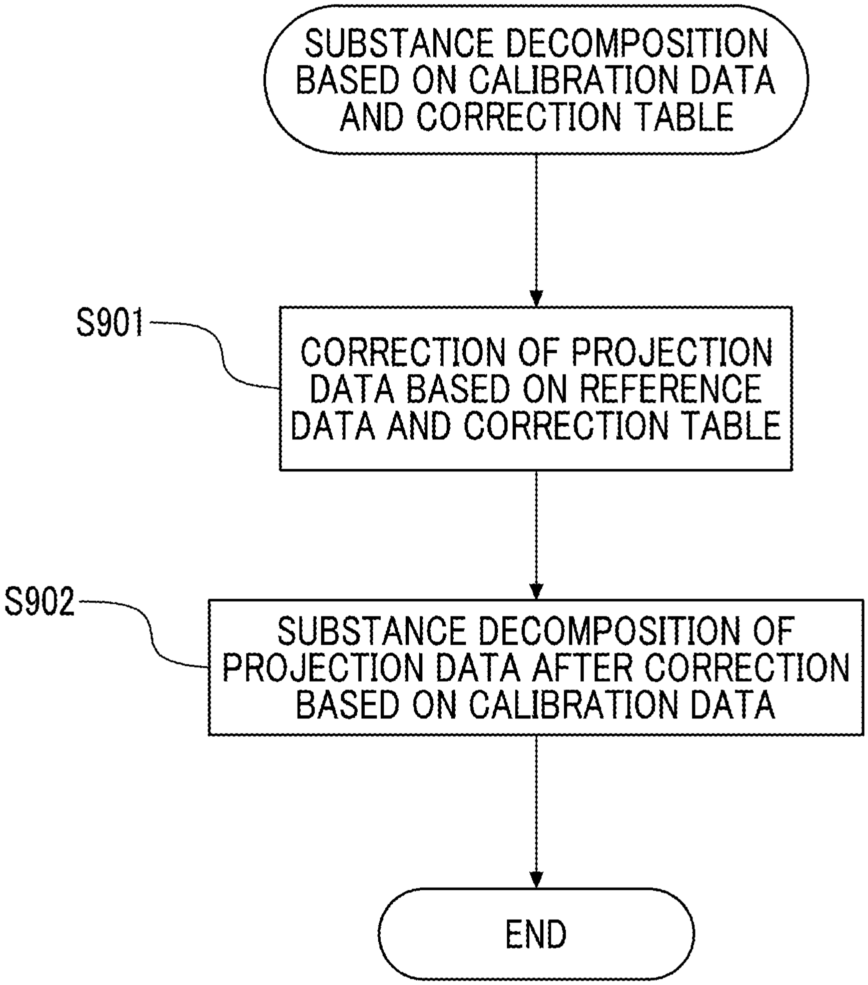
FIG. 9 is a diagram showing another example of a flow of processing of substance decomposition.

Another example of the flow of the processing of S602 will be described step by step with reference to FIG. 9.

S901

Figure 10:
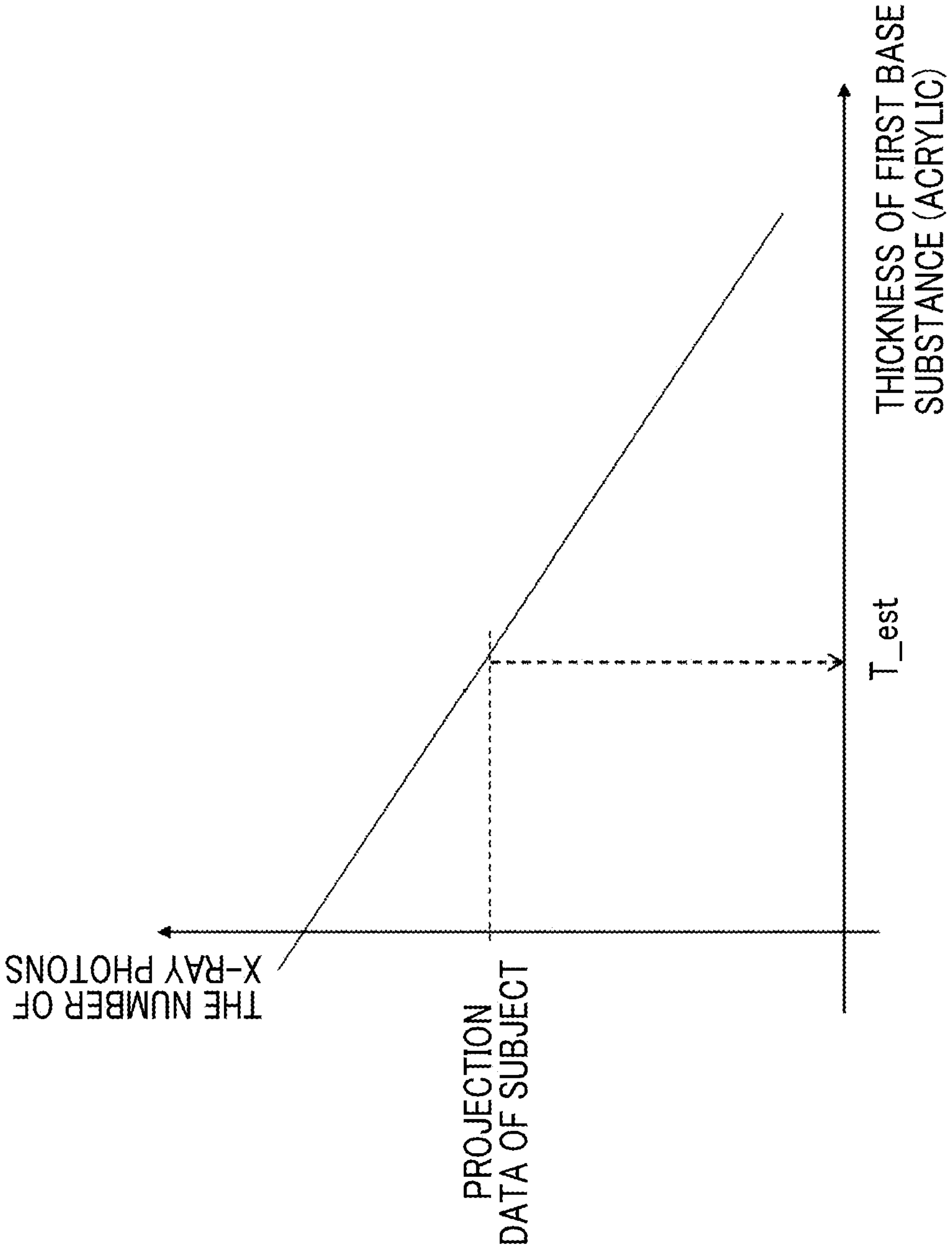
FIG. 10 is a diagram describing processing of obtaining an estimated thickness of a subject.

The operation device 108 corrects the projection data of the subject 106 based on the reference data acquired in S601 and the correction table. Specifically, first, a relationship between the thickness of the first base substance 301 and the total number of X-ray photons as shown in FIG. 10 is obtained using the data in which the thickness of the second base substance 302 is zero in the calibration data 303. Next, an estimated thickness T_est of the subject 106 is calculated by comparing the relationship illustrated in FIG. 10 and the projection data of the subject 106. Then, the correction coefficient with respect to the reference data is obtained for each energy bin from the correction table in the estimated thickness T_est, and the projection data of the subject 106 is corrected based on the obtained correction coefficient. That is, the projection data of the subject 106 including the fluctuation over time in the X-ray dose is divided by the correction coefficient for each energy bin, whereby the projection data of the subject 106 corresponding to the reference X-ray dose is calculated.

S902

The operation device 108 performs substance decomposition on the projection data corrected in S901 by using the calibration data 303. Specifically, first, the energy spectrum closest to the energy spectrum of the projection data corrected in S901 is selected from the calibration data 303. Then, substance decomposition is performed according to the thickness of the first base substance 301 and the thickness of the second base substance 302 corresponding to the selected energy spectrum to generate the projection data of the first base substance 301 and the projection data of the second base substance 302.

Through the flow of the processing described with reference to FIG. 9, substance decomposition is performed on the projection data of the subject 106 corrected based on the reference data and the correction table, based on the calibration data 303. Since the projection data of the subject 106 corrected based on the reference data and the correction table is used for the substance decomposition, the influence of pile-up that changes depending on the fluctuation over time in the X-ray dose or the difference in the radiation quality of the X-rays is reduced, and the accuracy of the substance decomposition can be improved. In addition, as compared to the flow of the processing described with reference to FIG. 7, a memory capacity used by the operation device 108 is smaller, and an operation time can be shortened. Return to the description of FIG. 6.

S603

The operation device 108 reconstructs a tomographic image for each substance by using the projection data on which substance decomposition is performed in S602. That is, a tomographic image of the first base substance 301 and a tomographic image of the second base substance 302 are reconstructed.

By the flow of the processing described with reference to FIG. 6, the tomographic image of the subject 106 is generated for each substance by using the projection data on which substance decomposition is performed based on the calibration data 303 and the correction table. Since the calibration data 303 and the correction table are used for the substance decomposition, the influence of pile-up that changes depending on the difference in the radiation quality of the X-rays is reduced, and the tomographic image subjected to the substance decomposition with high accuracy can be generated.

The example of the photon counting CT apparatus and the substance decomposition method according to the embodiment of the present invention have been described above. It should be noted that the present invention is not limited to the above-described example, and the components can be modified and embodied without departing from the gist of the invention. In addition, a plurality of components disclosed in the above-described example may be combined as appropriate. Further, some components may be deleted from all the components described in the above-described example.

EXPLANATION OF REFERENCES

101: photon counting CT apparatus
102: gantry
103: X-ray tube
104: bow tie filter
105: bed
106: subject
107: detector panel
107R: reference detector
108: operation device
109: input device
110: display device
111: X-ray
112: opening portion
300: calibration member
301: first base substance
302: second base substance
303: calibration data
P: detection element

What is claimed is:

1. A photon counting CT apparatus comprising:
an X-ray source that irradiates a subject with X-rays;
a photon counting type detector that detects the X-rays and outputs a signal, which corresponds to photon energies of the X-rays;
a computer configured by an execution of a program of instructions executable by the computer to perform a method comprising:
acquiring calibration data, which is an energy spectrum of X-rays transmitted through a calibration member including a combination of a first base substance and a second base substance having known substances and thicknesses;

changing an X-ray dose of X-rays irradiated by the X-ray source to the calibration member, and creating a correction table indicating a relationship between a number of X-ray photons and an X-ray dose for each energy bin based on the calibration data acquired while changing the X-ray dose of the X-rays irradiated by the X-ray source to the calibration member; and generating a tomographic image decomposed for each substance based on the calibration data and the correction table.

2. The photon counting CT apparatus according to claim 1, wherein the method performed by the computer further comprises:

correcting the calibration data based on the correction table and reference data including a fluctuation over time in an X-ray dose of X-rays irradiated by the X-ray source; and performing a substance decomposition on projection data of the subject by using the corrected calibration data.

3. The photon counting CT apparatus according to claim 1, wherein the method performed by the computer further comprises:

correcting projection data of the subject based on the correction table and reference data including a fluctuation over time in an X-ray dose of X-rays irradiated by the X-ray source; and performing a substance decomposition on the corrected projection data by using the calibration data.

4. The photon counting CT apparatus according to claim 1, wherein the energy spectrum of the X-rays transmitted through the calibration member is within a range of a fluctuation over time in an X-ray dose.

5. A substance decomposition method using a photon counting CT apparatus comprising an X-ray source that irradiates a subject with X-rays, and a photon counting type detector that detects the X-rays and outputs a signal corresponding to photon energies of the X-rays, the substance decomposition method comprising:

acquiring calibration data, which is an energy spectrum of X-rays transmitted through a calibration member including a combination of a first base substance and a second base substance having known substances and thicknesses;

changing an X-ray dose of X-rays irradiated by the X-ray source to the calibration member, and creating a correction table indicating a relationship between a number of X-ray photons and an X-ray dose for each energy bin based on the calibration data acquired while changing the X-ray dose of the X-rays irradiated by the X-ray source to the calibration member; and generating a tomographic image decomposed for each substance based on the calibration data and the correction table.

6. The substance decomposition method according to claim 5, further comprising:

correcting the calibration data based on the correction table and reference data including a fluctuation over time in an X-ray dose of X-rays irradiated by the X-ray source; and performing a substance decomposition on projection data of the subject by using the corrected calibration data.

7. The substance decomposition method according to claim 5, further comprising:

correcting projection data of the subject based on the correction table and reference data including a fluctuation over time in an X-ray dose of X-rays irradiated by the X-ray source; and performing a substance decomposition on the corrected projection data by using the calibration data.

8. The substance decomposition method according to claim 5, wherein the energy spectrum of the X-rays transmitted through the calibration member is within a range of a fluctuation over time in an X-ray dose.

* * * * *